United States Patent [19]
Thompson

[11] Patent Number: 5,372,251
[45] Date of Patent: Dec. 13, 1994

[54] SURGICAL SUTURE PACKAGE HAVING AN EMBOSSED PATTERN

[75] Inventor: Robert F. Thompson, Manchester, Mass.

[73] Assignee: American Cyanamid Co., Wayne, N.J.

[21] Appl. No.: 925,230

[22] Filed: Aug. 3, 1992

Related U.S. Application Data

[63] Continuation of Ser. No. 615,749, Nov. 16, 1990.

[51] Int. Cl.$^5$ .............. A61B 17/06; B65D 85/24
[52] U.S. Cl. .................... 206/63.3; 206/339; 206/388
[58] Field of Search .............. 206/63.3, 339, 388, 206/472, 49, 495, 232; 400/122, 127; 101/3.1, 28, 32; 493/405, 493; 162/109, 116; 428/180, 179; 156/209, 219; 40/124.1; 229/92.8

[56] References Cited

U.S. PATENT DOCUMENTS

| 348,671 | 9/1886 | Haehnlen | 206/495 X |
|---|---|---|---|
| 2,661,835 | 12/1953 | Grishaber | 206/472 X |
| 3,206,018 | 9/1965 | Lewis et al. | 206/63.3 |
| 3,779,375 | 12/1973 | Foster | 206/63.3 |
| 3,867,225 | 2/1975 | Nystrand | 428/180 X |
| 3,972,418 | 8/1976 | Schuler et al. | 206/339 X |
| 4,121,711 | 10/1978 | Bolanowski | 206/63.3 |
| 4,151,913 | 5/1979 | Freitag | 206/495 X |
| 4,284,194 | 8/1981 | Flatau | 206/63.3 |
| 4,518,643 | 5/1985 | Francis | 428/180 X |
| 4,574,948 | 3/1986 | Huck et al. | 206/63.3 |
| 4,699,271 | 10/1987 | Lincoln et al. | 206/63.3 |
| 4,859,094 | 8/1989 | Okada | 400/122 |
| 4,955,481 | 9/1990 | Novinski et al. | 206/472 X |
| 4,961,498 | 10/1990 | Kalinski et al. | 206/339 |
| 5,090,568 | 2/1992 | Tse | 206/472 X |
| 5,123,528 | 6/1992 | Brown et al. | 206/63.3 |

FOREIGN PATENT DOCUMENTS

| 2455880 | 12/1980 | France | A61B 17/06 |
|---|---|---|---|
| 2754936 | 6/1978 | Germany | 206/63.3 |
| 184947 | 8/1922 | United Kingdom | 206/63.3 |
| 2079250 | 1/1982 | United Kingdom | 206/495 |

*Primary Examiner*—Paul T. Sewell
*Assistant Examiner*—BethAnne Cicconi
*Attorney, Agent, or Firm*—C. F. Costello, Jr.

[57] ABSTRACT

An improved surgical suture package has a back panel and a cover flap foldably connected to one side of the back panel. The back panel and cover flap each have a coordinating surface. The improvement comprises a plurality of embossed patterns on the coordinating surfaces of the back panel and cover flap.

11 Claims, 3 Drawing Sheets

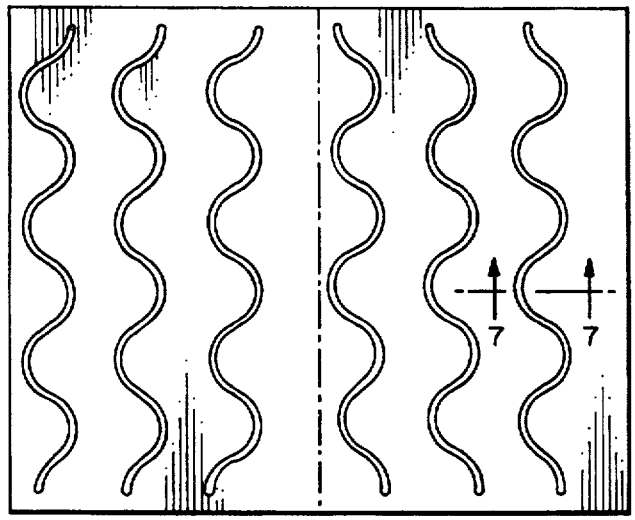
FIG. 7
FIG. 6
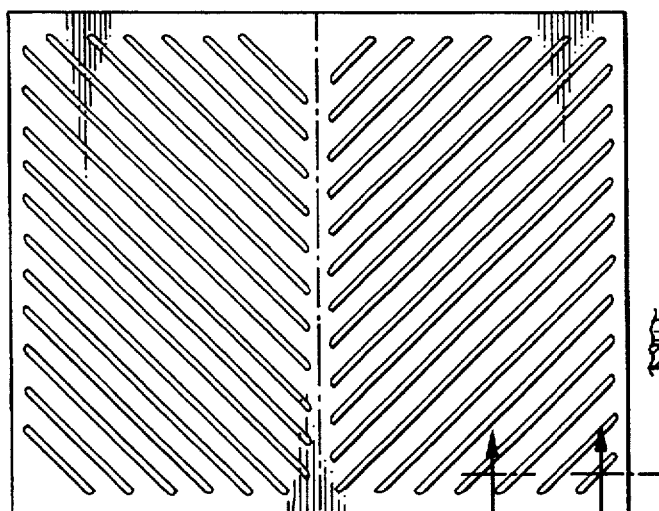
FIG. 9
FIG. 8

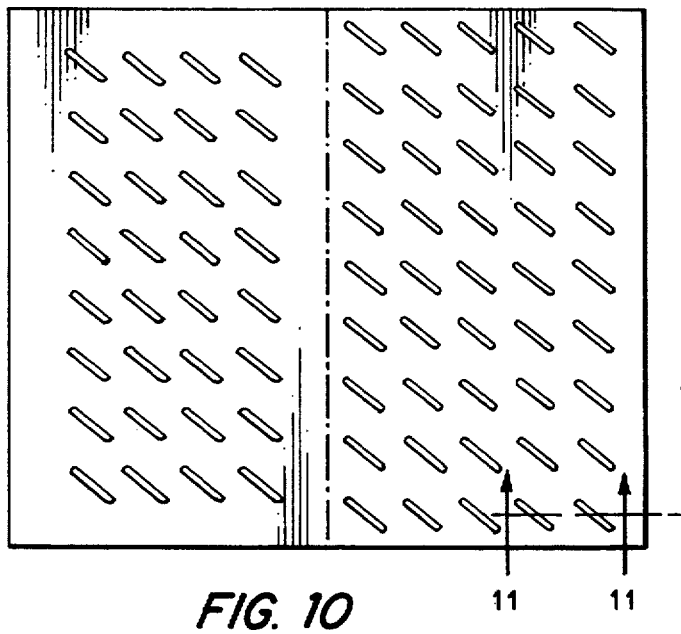
FIG. 10   FIG. 11
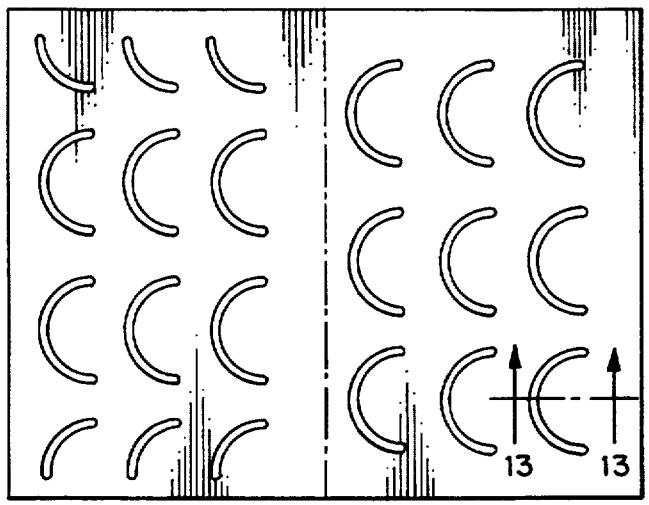
FIG. 12   FIG. 13

SURGICAL SUTURE PACKAGE HAVING AN EMBOSSED PATTERN

This is a continuation of co-pending application Ser. No. 07/615,749 filed on Nov. 16, 1990.

BACKGROUND AND SUMMARY OF THE INVENTION

This invention relates to an improved wound closure device package. The improvement comprises a plurality of embossed patterns. The wound closure device package can be a surgical suture package.

In one embodiment, the improved wound closure device package is a surgical suture package. The surgical suture package has a panel. The improvement is the surgical suture package manufactured from an irradiation sterilizable paper, and a plurality of embossed patterns on the panel. In a specific embodiment, the irradiation sterilizable paper is kraft paper.

In another embodiment, the wound closure device package has a back panel and a cover flap. The cover flap is foldably connected to one side of the back panel. The back panel and cover flap each have a coordinating surface. The improvement is a plurality of embossed patterns in columns on the coordinating surfaces of the back panel and cover flap. The number of columns on the back panel are less than the number of columns on the cover flap. In another improvement, the invention is a plurality of embossed patterns in rows on the coordinating surfaces of the back panel and cover flap, and as shown in FIG. 2 the rows of phantom embossed portions 4A on the back panel 1 are between the rows of embossed portions 5 on the cover flap 2.

In yet another embodiment, the improved wound closure device package is a surgical suture package having a back panel and a cover flap. The cover flap is foldably connected to one side of the back panel. The back panel and cover flap each have a coordinating surface. The improvement is the surgical suture package manufactured from an irradiation sterilizable paper and a plurality of embossed patterns. The embossed patterns are equally spaced on each of the coordinating surfaces of the back panel and cover flap. In a specific embodiment, the irradiation sterilizable paper is kraft paper.

In still another embodiment, the improved wound closure package is a surgical suture package having a back panel and a cover flap. The cover flap is foldably connected to one side of the back panel. The back panel and cover flap each have a coordinating surface. The improvement is the surgical suture package manufactured from an irradiation sterilizable material. The material is selected from metallic foil, polyolefin film and polyester film. The improvement also is a plurality of embossed patterns being equally spaced on each of the coordinating surfaces of the back panel and cover flap. In a specific embodiment, the irradiation sterilizable material is a laminated metallic foil.

In other specific embodiments, each of the embossed patterns is circular, linear, curvilinear or sinusoidal. In a more specific embodiment, the plurality of embossed linear patterns are parallel to each other.

In still yet another embodiment, the improved wound closure device package is a surgical suture package having a back panel and a cover flap. The cover flap is foldably connected to one side of the back panel by at least one score line. The back panel and the cover flap each have a coordinating surface. The improvement is the surgical suture package manufactured from an irradiation sterilizable paper and a plurality of embossed circular patterns. The embossed circular patterns are equally spaced on each of the coordinating surfaces of the back panel and cover flap. Also, the plurality of embossed circular patterns are in columns. The number of columns on the panel are less than the number of columns on the flap. In a specific embodiment, the irradiation sterilizable paper is kraft paper. In another specific embodiment, the plurality of embossed patterns on the back panel and cover flap are in rows. The rows on the back panel are between the rows on the cover flap.

In a still further embodiment, this improved wound closure device package is a surgical suture package having a back panel and a cover flap. The cover flap is foldably connected to one side of the back panel. The back panel and the cover flap each have a coordinating surface. The improvement comprises in combination, the surgical suture package manufactured from a chemically sterilizable material and a plurality of embossed patterns. The embossed patterns are equally spaced on each of the coordinating surfaces of the back panel and cover flap.

In a final embodiment, the improved wound closure device package is a surgical suture package having a back panel and a cover flap. The cover flap is foldably connected to one side of the back panel. The back panel and the cover flap each have a coordinating surface. The improvement comprises in combination, the surgical suture package manufactured from a chemically sterilizable paper and a plurality of embossed circular patterns. The embossed circular patterns are equally spaced on each of the coordinating surfaces of the back panel and cover flap. The plurality of embossed circular patterns are in columns. The number of columns on the back panel are less than the number of columns on the cover flap.

BRIEF DESCRIPTION OF THE DRAWINGS

FIGS. 6, 8, 10 and 12 are alternative front views of the suture package of FIG. 1; and FIGS. 7, 9, 11 and 13 are section views along the respective lines 7—7, 9—9, 11—11 and 13—13 of FIGS. 6, 8, 10 and 12.

DESCRIPTION OF THE INVENTION

Figure 1:
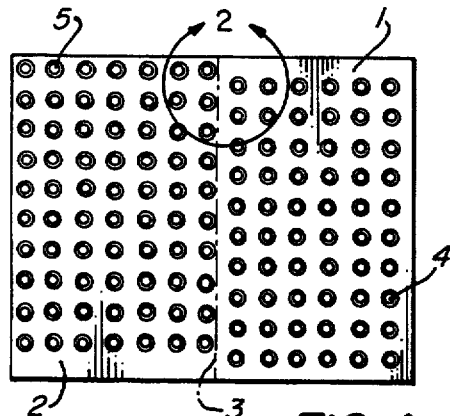
FIG. 1 is a front view of the suture package.

FIG. 1 describes the best mode of carrying out the invention at the time this application was filed. The intended use of the embodiment shown in FIG. 1 is as an interior card in a two part package. However, the embodiment shown in FIG. 1 can also be used as a component in a multicomponent package. The additional part or components of the package can be for a variety of purposes, e.g. visibility of the ends of the needled or non-needled surgical filaments, ease of bonding to make a sterile enclosure, and ease of dispensing the surgical filaments.

As an example of a two part package, please see U.S. Pat. No. 4,284,194, FIGS. 1 to 4d and the improvements thereof in U.S. Pat. Nos. 4,406,363 FIGS. 1 to 12; 4,413,727 FIGS. 1 to 5 and 8 to 13; and 4,708,241 FIGS. 1 to 7. The disclosure in U.S. Pat. No. 4,284,194 at column 4 lines 34 to 37 is material to the patentability of the inventions disclosed in this application. All of the above patents are incorporated herein by reference.

In this application, it is to be understood that the terms "suture package", "wound closure device package", or "surgical suture package" include the inventions as shown and described, either as an interior card, for example as described in U.S. Pat. No. 4,284,194 FIG. 1, or as a substitute for a foam member, for example as shown in U.S. Pat. No. 4,413,727 FIGS. 1 and 3, element 24 as one part of a two part package. These terms also include the inventions as shown and described as one component in a multicomponent package. Where designated and for contrast, a prior art two part or multicomponent package may also be described by these terms.

The package of this invention is useful in singly dispensing a braided wound closure device from a plurality of braided wound closure devices. The braided wound closure device is preferably a needled or non-needled suture, or ligature. Other wound closure devices, such as ligament or tendon prosthetic devices, may be singly dispensed from the package of this invention. This invention is also useful in dispensing a surgical suture or ligature from a suture package only containing a single suture or ligature. The single suture or ligature can be in the form of a monofilament or braid.

The package can be cutout and embossed from a sheet of irradiation and/or chemically sterilizable stock, for example surgical grade kraft paper. Chemical sterilization can be by using a fluid, e.g. ethylene oxide gas, which is sometimes abbreviated EtO. Various EtO sterilization processes are described in the prior art. For a background of the development of irradiation sterilization for medical devices generally and surgical sutures specifically, please see the monograph entitled "Radiosterilization of Medical Products 1974", International Atomic Energy Agency, Vienna, Austria, 1975, pages 431 to 435, which is incorporated herein by reference.

The package can also be cutout and embossed from an irradiation and/or chemically sterilizable metallic foil, such as aluminum. A stainless steel foil may also be useful. The metallic foil can be of a laminated construction for increased strength, rigidity and/or puncture resistance, or for other reasons. It is to be understood that the materials used to manufacture the metallic foil laminate, e.g. an adhesive, and a paper and/or a polymeric material are also to be irradiation and/or chemically sterilizable. A metallic foil laminated material is disclosed in U.S. Pat. No. 4,135,622, which issued Jan. 23, 1979. This patent is incorporated herein by reference.

Further, the package of this invention can be cutout and embossed from an irradiation and/or chemically sterilizable sheet or film of a polymeric material. The polymeric material may be natural, such as cellophane, or synthetic, such as a polyolefin. polyester or nylon. For a disclosure of a polyolefin suture package, please see "Two-Piece Tray Delivers Sutures, Speeds Surgery" by H. Forcinio in Food Drug Packaging vol. 48 no. 3, 1984, pages 5 and 46, which is incorporated herein by reference. The polyester can be polybutylene terephthalate or polyethylene terephthalate. A polyether-ester, such as polybutester, may also be useful. The polybutester can be a Hytrel TM polymer (Du Pont, Del., USA).

The apparatus and methods for making an embossed pattern on a foil, sheet or film are described in the prior art. How to make and how to use a two part or multicomponent suture package is also described in the prior art. Please see, e.g., U.S. Pat. No. 4,284,194. Therefore, a drawing of the improved suture package of this application beyond that described in the FIGS. 1 to 5 is not necessary for the understanding of how to make and/or how to use the subject matter sought to be patented.

The package as shown in FIG. 1 comprises a back panel 1 and a strand cover flap 2. The flap 2 is connected to the panel 1 by a score, perforation or similar line 3. The utility of the suture package is based on the embossed pattern, which is shown as circular portions 4 and 5. The function of the embossing is to provide a rough and/or irregular surface that will hold the one or more sutures in position within the package.

The function of the embossing also allows a single suture from a plurality of sutures to be dispensed from the package. The following theory, although not a part of this invention, is disclosed as one explanation for the single suture dispensing package. Static friction is greater than sliding (moving) friction. The force initially introduced to a single suture for dispensing, e.g., by pulling the suture with the thumb and index finger, is large enough to overcome the static friction of that one suture against the retainer and the other sutures. However, that one suture's sliding friction is not large enough to overcome the static friction of the other sutures against the retainer and against each other. Thus multiple surgical suture strands can be packaged together and directly dispensed singly without tangling. In this function, the embossing eliminates a foam layer or other dispensing member, both of which are known prior art means of singly dispensing a suture from a plurality of sutures. For example, please see respectively U.S. Pat. No. 4,284,194 FIG. 1a, element 2a and 4,533,041 FIG. 5, element 26. The U.S. Pat. No. 4,533,041 is incorporated herein by reference. The simplicity of the embossing in combination with a reduction of packaging materials and/or of complex manufacturing processes is an indicia of patentability of the inventions described in this application. The circular portions 4 and 5 describe the best mode of carrying out the inventions at the time this application was filed.

In one embodiment, the size, shape and volume of each circular portion 4 and 5, respectively on panel 1 and flap 2, is identical. The total number of circular portions 4 can be and preferably is different from the total number of circular portions 5.

In the embodiment shown in FIG. 1, the number of columns of circular portions 5 on flap 2 are one more in number than the number of columns of portions 4 on panel 1. With the proper spacing of each column and row of circular portions 4 and 5 on the respective panel 1 and flap 2, the circular portions 4 are located at the interstices of the circular portions 5 when the panel 1 and flap 2 are folded onto each other along the score or perforated line 3. As an example of proper spacing, please see FIG. 2. The phantom circular portions 4A describe the location of the circular portions 4 of label 1 after the panel 2 and label 1 are folded onto each other.

Figure 2:
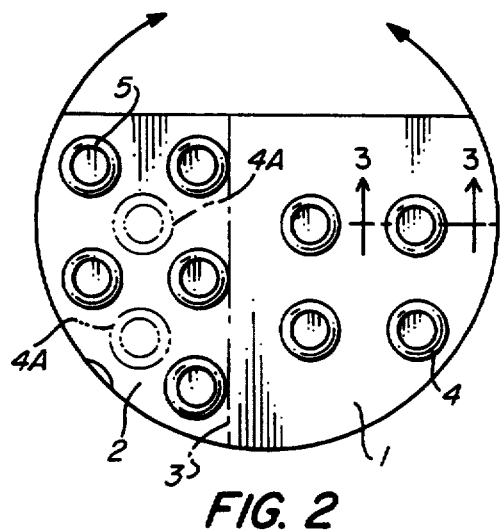
FIG. 2 is an expanded front view of the circled portion 2 of FIG. 1.
Figure 5:
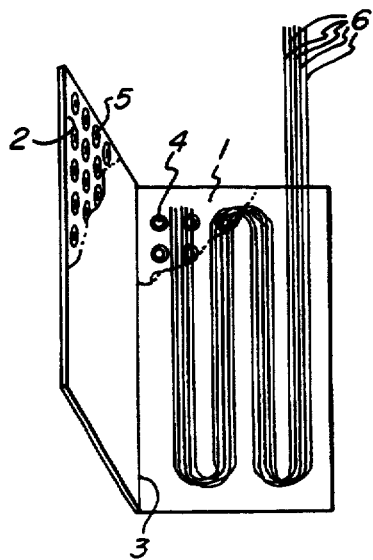
FIG. 5 is a cut away and perspective view of a partially folded package of FIG. 1, showing a plurality of surgical filaments.

Although the portions 4 and 5 shown in FIGS. 1, 2 and 5 are circular, it is to be understood that other patterns are within the scope of this invention. Such embossed patterns include, but are not limited to, elliptical, egg shaped, square and rectangular. The embossed patterns can also include a plurality of grooves having parallel and/or intercepting axes. The intercepting axes can be oblique or perpendicular to the parallel axes. The patterns can also be partial, e.g. semicircular, or curvilinear, e.g. sinusoidal. Further, it is to be understood that the embossed patterns can be concentric, including coaxial. Finally, a drawing of all of these other above-discussed patterns is not necessary for the understanding of the subject matter sought to be patented in this application.

Figure 4:
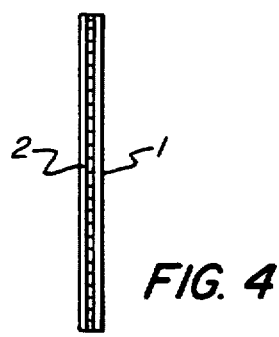
FIG. 4 is a right side view of a folded package of FIG. 1, showing the flap 2 folded onto the panel 1.
Figure 3:
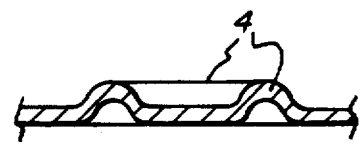
FIG. 3 is a section view along the line 3—3 of FIG. 2.

FIG. 3 is a section view of a circular portion 4 shown in FIG. 2. FIG. 4 is a right side view of a folded package of FIG. 1 showing the flap 2 folded onto the panel 1. As shown in FIG. 5, the surgical filaments 6 tend to flatten out both during and after being loaded into the package. In subsequent packaging or storing, the surgical filaments tend to further flatten out.

Referring again to FIGS. 1, 2 and 5, the distance between two adjacent columns of embossed patterns on the panel 1 and flap 2 is not critical to the practice of this invention. In many embodimnents, the phantom circular portions 4A (shown in FIG. 2) fit within the interstices of the circular portions 5 of flap 2 when the package is folded onto itself. It is also to be understood that in other embodiments the circular portions 4 on panel 1 can touch or overlap the portions 5 on flap 2 when the package is folded onto itself.

Referring to FIGS. 1 and 5, in one embodiment the number of columns of embossed patterns on panel 1 (there are six columns shown in FIG. 1) is equal to or greater than the number of passes of surgical filaments 6 loaded into the package (there are four passes shown in FIG. 5). In another embodiment, the number of rows on the panel 1 and flap 2 (there are ten rows shown for each in FIG. 1) be at least equal to the number of passes for the plurality of filaments in the package. As used in this application, the term "column" means a single line of circular portions 4 and/or 5 that are parallel to the score line 3; the term "row" means a single line of concentric portions 4 and/or 5 that are parallel to the top and bottom of the package shown in FIG. 1.

As shown in FIGS. 1 and 5, the rows and columns of the circular portions 4 and 5 are equally spaced in the respective panel 1 and flap 2. However, unequal spacing may also be useful in practicing this invention, which any person skilled in the surgical filament art can conclude without undue experimentation.

It is to be understood that a prior art suture package can be improved by a plurality of embossed patterns on a single card, for example the circular portions 4 on back panel 1 in FIG. 1, being inserted adjacent to a single suture. This improvement can be especially useful in ophthalmic suture packages because an ophthalmic suture is usually of a fine denier and may "drift" in the package. The improved embodiment of this invention can stabilize the ophthalmic suture and therefore make it easier to be located and dispensed. As an example of this improved embodiment, the plurality of embossed patterns on a single card can be placed on center panel 17 in FIG. 2 of U.S. Pat. No. 4,412,613. The flap 17a can then be folded onto the single card as shown in FIG. 4 of this patent, which is incorporated herein by reference.

It is also to be understood that the peripheral edges of either or both of the panel 1 and flap 2 in this application can contain additional flaps, panels or tabs, and/or the panel 1 and flap 2 can be of a different configuration than that shown in FIG. 1. Other modes are embodied in the invention described in this application. For example, referring to FIGS. 1 and 5, the suture package can comprise a plurality of embossed patterns on either the back panel 1 or strand cover flap 2.

I claim:

1. An article of manufacture comprising a first part consisting essentially of an outer sealed envelope having at least one edge and means adjacent the at least one edge for opening the outer sealed envelope, and contained therein a second part having a sterile, surgical suture package, the surgical suture package having a back panel and a cover flap foldably connected to one edge of the back panel, said back panel and the cover flap each having a facing side when said surgical suture package is folded on the one edge, the improvement consisting of in combination, said surgical suture package manufactured from a chemically sterilizable material and a plurality of embossed patterns being equally spaced on each of the facing sides of said back panel and cover flap, at least two surgical suture strands contained on said back panel, and said cover flap laid onto the at least two surgical suture strands and said back panel with at least an end of each of said strands external to said back panel and cover flap, such that when said outer sealed envelope is opened, a single suture can be grasped and directly dispensed from said package.

2. An article of manufacture comprising a first part consisting essentially of an outer sealed envelope having at least one edge and means adjacent the at least one edge for opening the outer sealed envelope, and contained therein a second part having a sterile, surgical suture package, the surgical suture package having a back panel and a cover flap foldably connected to one edge of the back panel, said back panel and the cover flap each having a facing side when said surgical suture package is folded on the one edge, the improvement consisting of in combination, said surgical suture package manufactured from a chemically sterilizable paper and a plurality of embossed circular patterns being equally spaced on each of the facing sides of said back panel and cover flap, the plurality of embossed circular patterns being in columns, the number of columns on said panel being less than the number of columns on said flap, at least two surgical suture strands contained on said back panel, and said cover flap laid onto the at least two surgical suture strands and said back panel with at least an end of each of said strands external to said back panel and cover flap, such that when said outer sealed envelope is opened, a single suture can be grasped and directly dispensed from said package.

3. An article of manufacture comprising a first part consisting essentially of an outer sealed envelope having at least one edge and means adjacent the at least one edge for opening the outer sealed envelope, and contained therein a second part having a sterile, wound closure device package, the wound closure device package having a back panel and a cover flap foldably connected to one edge of the back panel, said back panel and cover flap each having a facing side when said wound closure device package is folded on the one edge, the improvement consisting of a plurality of embossed patterns in columns on the facing sides of said back panel and cover flap, and the number of columns on said panel being less than the number of columns on said flap, at least two surgical suture strands contained on said back panel, and said cover flap laid onto the at least two surgical suture strands and said back panel with at least an end of each of said strands external to said back panel and cover flap, such that when said outer sealed envelope is opened, a single suture can be grasped and directly dispensed from said package.

4. An article of manufacture comprising a first part consisting essentially of an outer sealed envelope having at least one edge and means adjacent the at least one edge for opening the outer sealed envelope, and contained therein a second part having a sterile, wound closure device package, the wound closure device package having a back panel and a cover flap foldably connected to one edge of the back panel such that said back panel and cover flap each having a facing side when said wound closure device package is folded on the one edge, the improvement consisting of a plurality of embossed patterns in rows on each of the facing sides of said back panel and cover flap, and the plurality of embossed patterns in rows on said back panel being between the plurality of embossed patterns in rows on said cover flap, at least two surgical suture strands contained on said back panel, and said cover flap laid onto the at least two surgical suture strands and said back panel with at least an end of each of said strands external to said back panel and cover flap, such that when said outer sealed envelope is opened, a single suture can be grasped and directly dispensed from said package.

5. An article of manufacture comprising a first part consisting essentially of an outer sealed envelope having at least one edge and means adjacent the at least one edge for opening the outer sealed envelope, and contained therein a second part having a sterile, surgical suture package, the surgical suture package having a back panel and a cover flap foldably connected to one edge of the back panel, said back panel and cover flap each having a facing side when said surgical suture package is folded on the one edge, the improvement consisting of said surgical suture package manufactured from an irradiation sterilizable material selected from the group consisting of polyolefin film and polyester film, and a plurality of embossed patterns being equally spaced on each of the facing sides of said back panel and cover flap, at least two surgical suture strands contained on said back panel, and said cover flap laid onto the at least two surgical suture strands and said back panel with at least an end of each of said strands external to said back panel and cover flap, such that when said outer sealed envelope is opened, a single suture can be grasped and directly dispensed from said package.

6. An article of manufacture comprising a first part consisting essentially of an outer sealed envelope having at least one edge and means adjacent the at least one edge for opening the outer sealed envelope, and contained therein a second part having a sterile, surgical suture package, the surgical suture package having a back panel and a cover flap foldably connected to one edge of the back panel, said back panel and cover flap each having a facing side when said surgical suture package is folded on the one edge, the improvement consisting of said surgical suture package manufactured from metallic foil, and a plurality of embossed patterns being equally spaced on each of the facing sides of said back panel and cover flap, at least two surgical suture strands contained on said back panel, and said cover flap laid onto the at least two surgical suture strands and said back panel with at least an end of each of said strands external to said back panel and cover flap, such that when said outer sealed envelope is opened, a single suture can be grasped and directly dispensed from said package.

7. The article of claim 1 wherein each of the embossed patterns is circular.

8. The article of claim 1 wherein each of the embossed patterns is linear.

9. The article of claim 8 wherein the plurality of embossed patterns are parallel to each other.

10. The article of claim 1 wherein each of the embossed patterns is curvilinear.

11. The article of claim 10 wherein each of the embossed patterns is sinusoidal.

* * * * *